United States Patent [19]

King

[11] Patent Number: 4,533,658

[45] Date of Patent: Aug. 6, 1985

[54] INSECTICIDAL 3-ALKYL-5-(ALKOXY- OR ALKYLTHIO-PHOSPHYNYL OR PHOSPHINOTHIOYL-THIOMETHYL)-1,2,4-OXADIAZOLES

[75] Inventor: William F. King, Novato, Calif.

[73] Assignee: Chevron Research Company, San Francisco, Calif.

[21] Appl. No.: 601,889

[22] Filed: Apr. 19, 1984

Related U.S. Application Data

[63] Continuation of Ser. No. 322,995, Nov. 19, 1981, abandoned.

[51] Int. Cl.³ .................. A01N 57/24; C07F 9/65
[52] U.S. Cl. ........................ 514/92; 548/119
[58] Field of Search ............... 548/119; 424/200

[56] References Cited

U.S. PATENT DOCUMENTS 3,432,519 3/1969 Metivier et al. ............. 548/119
4,110,336 8/1978 Mildenberger ............... 548/119

FOREIGN PATENT DOCUMENTS 2919621 11/1980 Fed. Rep. of Germany .
1213707 11/1970 United Kingdom .

*Primary Examiner*—Richard L. Raymond
*Attorney, Agent, or Firm*—S. R. LaPaglia; T. G. DeJonghe; S. L. Biggs

[57] ABSTRACT

Oxadiazole compounds of the formula

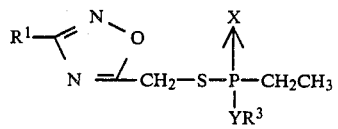

wherein X is sulfur or oxygen; Y is sulfur or oxygen; $R_1$ is methyl, ethyl isopropyl or cyclopropyl; and $R_2$ is ethyl or isopropyl, provided that when $R_1$ is methyl or ethyl, $R_2$ is not ethyl, are effective as corn root worm insecticides.

15 Claims, No Drawings

INSECTICIDAL 3-ALKYL-5-(ALKOXY- OR ALKYLTHIO-PHOSPHYNYL OR PHOSPHINOTHIOYL-THIOMETHYL)-1,2,4-OXADIAZOLES

This is a continuation of application Ser. No. 322,995, filed Nov. 19, 1981, abandoned.

BACKGROUND OF THE INVENTION

This invention relates to certain novel 3-alkyl-5-(alkoxy- or alkylthio-phosphynyl or phosphinothioylthiomethyl)-1,2,4-oxadiazoles and their use as soil insecticides to combat corn root worm. In particular I have found that the compounds of this invention show surprisingly good activity in killing Diabrotica larvae.

German Offenlegungsschrift No. 2,919,621 discloses insecticidal compounds of the general formula:

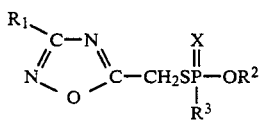

wherein X is oxygen or sulfur; $R_1$ is hydrogen, $C_1$ to $C_4$ alkyl optionally substituted with halogen, $C_1$ to $C_3$ alkoxy, or phenyl; $R_2$ is $C_1$ to $C_4$ alkyl; and $R_3$ is $C_1$ to $C_4$ alkyl, $C_1$ to $C_6$ alkylamino, allylamino or di-($C_1$ to $C_3$) alkylamino where the two alkyl groups on the nitrogen may form a 5- or 6-membered ring which optionally may contain an oxygen atom.

The compounds of the German Offenlegungsschrift were disclosed as effective against "sucking" and "biting" insects as well as mites and ticks of the order Acarina. The examples showed testing certain of the compounds for insecticidal activity on red spider mites, bean aphids, houseflies, German cockroach, Mexican bean beetle larvae, corn beetle larvae, flour weevils and African boll weevil larvae.

Commonly-assigned, U.S. Pat. No. 4,237,121 discloses the use of corn root worm insecticides of compounds of the formula:

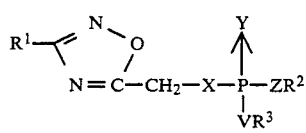

wherein X, Y, Z and V are sulfur or oxygen and $R^1$, $R^2$, $R^3$ are alkyl of 1 to 4 carbon atoms.

Commonly-assigned U.S. Pat. No. 4,213,973 discloses the use of compounds of the formula

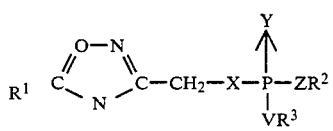

wherein X, Y, Z and V are oxygen or sulfur; $R_1$ is hydrogen or alkyl of 1 to 6 carbon atoms and $R^2$ and $R^3$ are alkyl of 1 to 6 carbon atoms, as corn root worm insecticides.

U.S. Pat. No. 3,432,519 discloses insecticidal and acaricidal compounds of the general formula

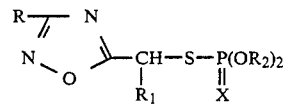

wherein R represents a hydrogen atom, an alkyl group containing 1 to 6 carbon atoms optionally carrying an alkoxy substituent containing 1 to 4 carbon atoms or an aryl group (preferably phenyl) which may carry one or more substituents selected from hydrogen atoms, the nitro group and alkyl, alkoxy and alkylthio groups containing 1 to 4 carbon atoms, $R_1$ represents a hydrogen atom or an alkyl group containing 1 to 4 carbon atms, $R_2$ represents an alkyl group containing 1 to 4 carbon atoms and X represents an oxygen or sulfur atom.

British Pat. No. 1,213,707 discloses insecticidal compounds of the general formula

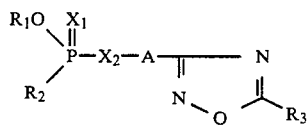

wherein $X_1$ and $X_2$ which may be the same or different, each represents an oxygen or sulfur atom; A represents an alkylene group; $R_1$ represents an alkyl group, $R_2$ represents an alkyl or alkoxy group; and $R_3$ represents a hydrogen atom or an optionally substituted carbamoyl or amino group.

The examples of the British patent show testing of certain of the compounds for insecticidal activity on adult houseflies; mosquito larvae, diamond back moth larvae, aphids and adult mustard beetles; red spider mites; and white butterfly larvae. None of these tests involved application and use of the insecticide in the soil habitat of the insects.

U.S. Pat. No. 4,028,377 discloses insecticidal compounds of the general formula:

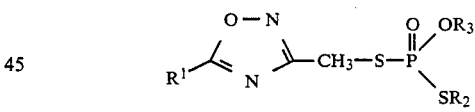

wherein $R_1$ represents hydrogen, unsubstituted alkyl, benzyl or phenyl, $R_2$ represents methyl or ethyl, and $R_3$ represents unsubstituted $C_1$-$C_7$ alkyl optionally interrupted by oxygen or represents $C_3$-$C_4$ alkenyl.

The examples of the U.S. Pat. No. 4,028,377 show testing of certain of the compounds for insecticidal activity on ticks in cotton wool; larvae of ticks; mites; and on root-gall-nematodes in soil. In the latter test, the soil infested with the root-gall-nematodes was treated with the compounds to be tested and then tomato seedlings were planted either immediately after the soil preparation or after 8 days waiting.

British Pat. No. 1,261,158 discloses compounds of the general formula:

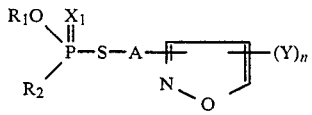

wherein $R_1$ represents an alkyl group, $R_2$ represents an alkyl or alkoxy group, X represents an oxygen or sulfur atom; A represents a saturated divalent aliphatic hydrocarbyl group; Y represents a halogen atom or an alkyl or alkoxy carbonyl group; and n is 0, 1 or 2. The compounds of the examples of British Pat. No. 1,261,158 were tested for insecticidal effectiveness on flies, mosquito larvae, moth larvae, mustard beetles, aphids, spider mites and butterfly larvae.

As described in the Ortho Seed Treater Manual, copyright 1976, Chevron Chemical Company, page 27, corn root worms have been controlled with chlorinated hydrocarbon insecticides, but in areas where resistance to such treatment has developed, good control has been obtained with organic phosphorus or carbamate soil insecticides such as Diazinon and Carbofuran insecticides. The chemical names and formulas for these latter insecticides are given below:

Diazinon insecticide: O,O—diethyl O—(2-isopropyl-4-methyl-6-pyrimidinyl)phosphorothioate

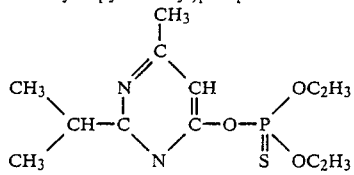

Carbofuran insecticide: 3,3-dihydro-2,2-dimethyl-7-benzofuranyl-methylcarbamate

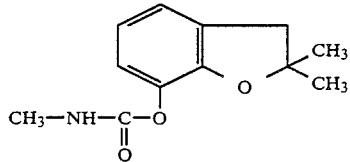

SUMMARY OF THE INVENTION

The 3-alkyl-5-(alkoxy- or alkylthio-phosphynyl or phosphinothioyl-thiomethyl)-1,2,4-oxadiazole compounds of this invention are represented by the formula:

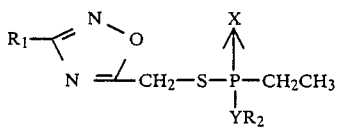

wherein X is sulfur or oxygen, Y is sulfur or oxygen, $R_1$ is methyl, ethyl, isopropyl, or cyclopropyl and $R_2$ is ethyl or isopropyl, provided that when $R_1$ is methyl or ethyl, $R_2$ is not ethyl.

Among other factors, the present invention is based on my finding that the substituted oxadiazole compounds of my invention are surprisingly effective as insecticides for killing corn root worms. The compounds are very effective in killing corn root worms when applied to their soil habitat. This is especially surprising, since certain closely related compounds have shown poor activity as insecticides against corn root worm.

Preferred compounds include those where X is sulfur, $R_1$ is methyl or ethyl and $R_2$ is isopropyl.

As used herein, the following terms have the following meanings, unless expressly stated to the contrary.

The term "root worm" is used herein to include the Northern, Southern and Western species of the corn root worm. All of these are of the Diabrotica genus. The scientific name of the Northern species is *Diabrotica longicornis*, the scientific name of the Southern species is *Diabrotica undecimpunctata howardi*, and the scientific name of the Western species is *Diabrotica virgifera*.

DETAILED DESCRIPTION OF THE INVENTION

The compounds used in the present invention may be prepared by subjecting the appropriate 3-alkyl-5-chloro-1,2,4-oxadiazoles (II) to a phosphorylation reaction.

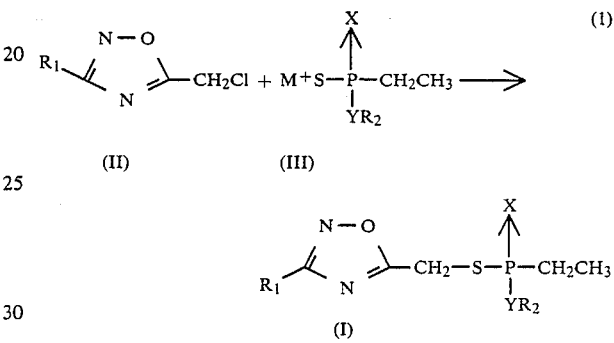

The phosphinate salts have the general formula (III) wherein X, Y and $R_2$ are as previously defined and M is a group IA metal cation or $NH_4^+$. The phosphorylation reaction may be carried out in an inert organic solvent such as methyl ethyl ketone, acetone, acetonitrile, ether, methanol or benzene. Preferably, equimolar amounts of reactants are employed, although a small excess of either may be used. Either reactant may be added to the other reactant in the solvent; however, it is preferred to add the solid phosphinate salt to a solution of the 3-alkyl-5-chloromethyl)-1,2,4-oxadiazole (II). The addition is carried out at temperatures in the range of 15° to 30° C. Upon completion of addition of the salt, the temperature of the salt is raised, preferably to about 50° C.; the reaction mixture is then stirred until the reaction is complete, about 1 to about 24 hours.

At completion of the reaction, the solvent is stripped under reduced pressure. The product, a liquid, is then isolated by conventional procedures such as extraction, chromatography, filtration.

The salts used in the phosphorylation reaction may be prepared according to the reaction scheme:

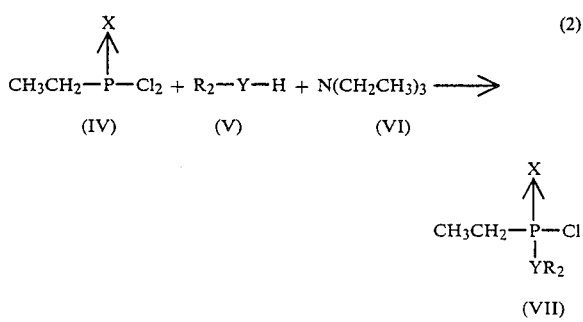

-continued

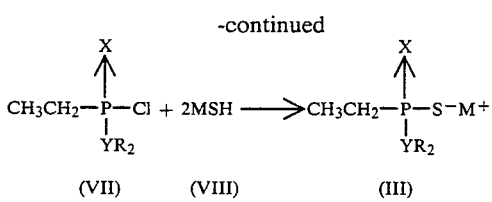

wherein X, Y and $R_2$ are as defined in conjunction with Formula I and M is a group IA (alkali) metal cation or $NH_4^+$.

Reaction (2) is carried out by adding an approximately equimolar amount of V to a stirred solution of IV in benzene. An approximately equimolar amount of VI was slowly added in a dropwise amount over a period of from about 0.5 to 1 hour. After the addition was complete, the reaction mixture was stirred for an extended period of time, about 16 hours, filtered and the solvent stripped. Other inert organic solvents such as toluene may be used in place of benzene.

The MSH used in reaction (3) is prepared in situ by dissolving MOH in isopropyl alcohol by stirring, followed by a period of additional stirring from about 2 to 4 hours. Hydrogen sulfide (gas) was added by bubbling it through the MOH-alcohol mixture. The resulting mixture was then stirred for about 2 to 4 hours to give the (VIII).

Reaction (3) was carried out by adding product VII (of Reaction (2)) to mixture VIII in a ratio of about two equivalents of VIII per equivalent of VII in several portions. The reaction mixture was stirred for an extended period of time, about 5 to about 12 hours, and then refluxed for about 1 to about 3 hours. The solvent was stripped, and toluene was used to chase the solvent. The product, (III), was washed with hexane and ethyl ether.

The 3-alkyl-5-chloromethyl-1,2,4-oxadiazoles, II, used in the preparation of the compounds of this invention may be prepared by the condensation of the appropriate alkylamidoximes with alpha-chloroacetyl chloride according to the following reaction scheme:

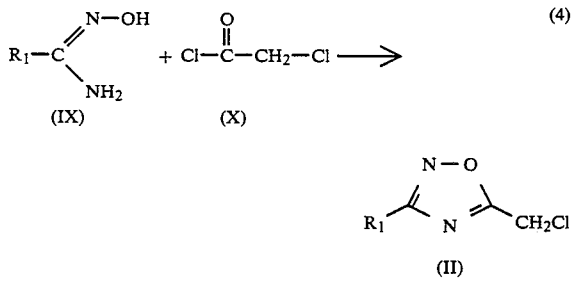

wherein $R_1$ is as previously defined in connection with Formula I. Further details of this preparation are disclosed in commonly-assigned U.S. Pat. No. 4,237,121 to King and Wheeler, which is incorporated by reference.

An alternate method of preparing the oxadiazole intermediates of formula II which is suitable for the large scale production of such compounds and which produces those intermediates in increased yields is disclosed in the commonly-assigned, copending U.S. patent application of R. N. Reynolds titled "Process for Preparing 5-Halomethyl-1,2,4-Oxadiazoles and Intermediates Therefor."

In the use of the compounds of my invention as corn root worm insecticides, optimum formulation concentrations and the manner and frequency of application may vary somewhat with the particular species of corn root worm, the degree of infestation, the environment, including type of soil, soil conditions and weather conditions (e.g. rain fall), and can be obtained by routine experimentation.

A further understanding of my invention can be had from the following non-limiting examples.

EXAMPLE 1

Preparation of Ethyl-O-isopropyldithiophosphinate Potassium Salt

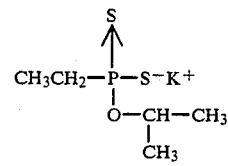

To a stirred mixture of 74.2 g (0.455 moles)

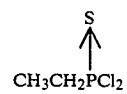

Ethylthiophosphoric acid dichloride in 400 ml benzene, 30.1 g (0.5 moles) isopropyl alcohol was added. To that mixture 50.6 g (0.5 moles) triethylamine was added at a dropwise rate overnight. The mixture was then warmed for about 1 hour. The mixture was filtered by gravity. Most of the solvent (benzene) was stripped off under reduced pressure and heat to give

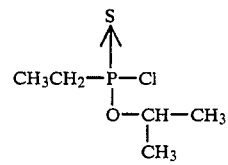

The KSH was prepared in situ by the following procedure: 56.5 g (1 mole) KOH was dissolved in about 350 ml isopropyl alcohol with stirring; the mixture was allowed to stir for about 2 hours. $H_2S$ was added to the mixture by bubbling the gas through it (about 35 g). The resulting KSH mixture was then allowed to stir for 1 hour.

To the KSH mixture, the product of the first step,

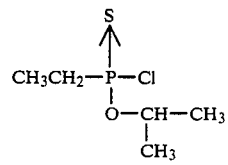

was added in several portions, cooling the reaction mixture with water if needed. The reaction mixture was stirred overnight and then refluxed for two hours. The solvent was removed under reduced pressure and toluene was used to chase the solvent. The product was then washed with hexane:ethyl ether (3:2).

The salts used to make the compounds in Table I may be prepared according to the above procedure. Optionally, an NaSH mixture is substituted for the KSH mixture.

EXAMPLE 2

Preparation of

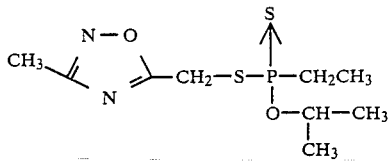

To about 75 ml methyl ethyl ketone, 3.3 g (0.025 moles) 3-methyl-5-chloromethyl-1,2,4-oxadiazole and 6.7 g (0.03 moles) of the product of Example 1 were added with stirring. The reaction mixture was heated to about 55° C. with stirring for 6 hours. The methyl ethyl ketone was stripped under reduced pressure to give the crude product. Water (about 50 ml) and methylene chloride (about 75 ml) were added to the product and the resulting mixture stirred. The product was extracted into the methylene chloride and washed twice with 50 ml water. The product was separated with the methylene chloride (organic) phase. Magnesium sulfate was added to the methylene chloride phase to dry it. Filtering of the methylene chloride phase followed by chromatography on silica gel eluting with hexane and methylene chloride, yielded 6.4 g of the product, a light yellow liquid.

Elemental analysis for $C_9H_{17}N_2O_2PS_2$ showed: calculated %C 38.6, %H, 6.11, and %N 9.99; found %C 40.8, %H 6.43, and %n 10.08.

EXAMPLE 3

Preparation of

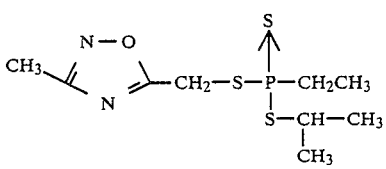

To 75 ml methyl ethyl ketone, 3.3 g (0.025 moles) 3-methyl-5-chloromethyl-1,2,4-oxadiazole and 7.2 g (0.03 moles) ethyl-S-isopropyldithiophosphinate potassium salt were added with stirring. The reaction mixture was heated to 55° C. with stirring for 6 hours. The methyl ethyl ketone was stripped under reduced pressure to give the crude product. Water (about 50 ml) and methylene chloride (about 75 ml) were added to the product and the mixture was stirred for about 10 min. The aqueous and methylene chloride phases were separated, the product separating with the methylene chloride phase. The methylene chloride phase was dried with magnesium sulfate and filtered to give 5.2 g of the product, a yellow liquid which was chromatographed on silica gel and eluted with hexane:methylene chloride (1:1).

Elemental analysis for $C_9H_{17}N_2OPS_3$ showed: Calculated %C 36.5, %H 5.78, and %N 9.45; found %C 38.6, %H 6.05, and %N 10.85.

EXAMPLE 4

Preparation of

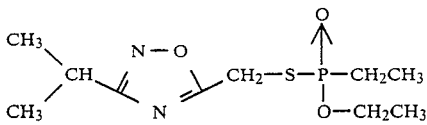

To 75 ml acetone, 2.8 g 3-isopropyl-5-chloromethyl-1,2,4-oxadiazole was added and the resulting mixture stirred for a few minutes. To that mixture 2.9 g

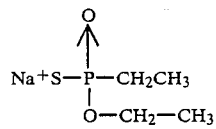

Ethyl-O-ethylthiophosphinate sodium salt was added and the resulting mixture stirred for about 10 minutes and then refluxed for about 4 hours. The reaction mixture was then stirred overnight. The acetone was stripped under reduced pressure to give the crude product. Methylene chloride (about 75 ml) and water (about 50 ml) were added. The water served to wash the product, removing NaCl resulting from the reaction. The aqueous and methylene chloride phases were separated, the product separating with the methylene chloride phase. The methylene chloride phase was dried with magnesium sulfate. The product was obtained by column chromatography of the methylene chloride phase, eluting first with hexane and then hexane:methylene chloride (1:1).

Elemental analysis for $C_{10}H_{19}N_2O_3PS$ showed: calculated %C 43.16, %H 6.88, and %N 10.07; found %C 42.82, %H 6.91, and %N 10.62.

Compounds made in a manner consistent with Examples 1 to 4 are found in Table I.

EXAMPLE 5

Control of Diabrotica Larvae

A number of the compounds of the present invention were evaluated for control of Diabrotica larvae by the following procedure:

For each test compound, a dilution series to give 6.4, and 2.5 ppm (weight:weight) active ingredient in soil was prepared by diluting an acetone-test compound mixture with the appropriate amount of water containing a small amount of Ortho X-77 nonionic spreader.

A 300 g batch of soil was treated with a test compound mixture to give the appropriate concentration in soil (i.e. 6.4, 2.5 or 1 ppm).

About 20 two- to four-day old Diabrotica eggs were placed in the bottom on three 8 oz. plastic cups. Half of the treated soil was evenly split between the three cups. Ten corn seeds which have been pre-soaked in water were evenly distributed on top of the soil in each cup. Ten ml of water was gently added to each cup and the remaining soil divided equally between the three cups, thus covering the corn seeds. The soil surface of the cups was lightly sprayed with water to provide a water seal on each cup. The cups were incubated at 70° F. for 10 days, with daily watering.

After 10 days, each test cup was examined under a dissecting scope by observing the corn roots and soil through the clear plastic walls of the cup. Control of newly-hatched larvae was evaluated by visually evaluating the degree of corn root damage by feeding larvae in conjunction with the visible presence of live and/or dead larvae.

The compounds tested, the concentration of test compound in soil (ppm) and percent control of Diabrotica larvae are given in Table II.

I have found from the results of biological testing that certain relatively closely related compounds showed no or poor effectiveness in controlling corn root worm as measured by the test of Example 5. Some of those compounds are shown in Table III, and such compounds are accordingly excluded from the scope of the present invention.

TABLE I

Compounds of the Formula

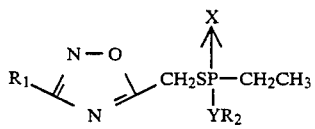

| Compound No. | X | Y | $R_1$ | $R_2$ | Physical State | ELEMENTAL ANALYSIS | | | | | |
|---|---|---|---|---|---|---|---|---|---|---|---|
| | | | | | | % Carbon | | % Hydrogen | | % Nitrogen | |
| | | | | | | Calc. | Fd. | Calc. | Fd. | Calc. | Fd. |
| 1 | S | O | $-CH_3$ | $-CH(CH_3)_2$ | Yellow liquid | 38.6 | 40.8 | 6.11 | 6.43 | 9.99 | 10.1 |
| 2 | S | O | $-CH_2CH_3$ | $-CH(CH_3)_2$ | Yellow liquid | 40.79 | 39.88 | 6.51 | 6.23 | 9.52 | 9.74 |
| 3 | S | S | $-CH_3$ | $-CH(CH_3)_2$ | Yellow liquid | 36.5 | 38.6 | 5.78 | 6.05 | 9.45 | 10.9 |
| 4 | S | S | $-CH_2CH_3$ | $-CH(CH_3)_2$ | Amber liquid | 38.7 | 41.3 | 6.17 | 6.47 | 9.03 | 10.7 |
| 5 | O | O | $-CH(CH_3)_2$ | $-CH_2CH_3$ | Colorless liquid | 43.16 | 42.82 | 6.88 | 6.91 | 10.07 | 10.62 |
| 6 | S | O | $-CH(CH_3)_2$ | $-CH_2CH_3$ | Yellow liquid | 40.8 | 41.3 | 6.51 | 7.05 | 9.52 | 10.4 |

TABLE II

| Compound No. | ppm | Soil Treatment % Control | | |
|---|---|---|---|---|
| | | Day 0 | Day 17 | Day 31 |
| 1 | 6.4 | 100 | 95.5 | — |
| | 2.5 | 97.5 | 93.5 | — |
| | 6.4 | 100 | | 96 |
| | 2.5 | 96 | | 94 |
| 2 | 6.4 | 62 | | 99.2 |
| | 6.4 | 100 | | |
| | 2.5 | 100 | | |
| | 2.5 | 2.5 | | 100 |
| 3 | 6.4 | 100 | | |
| | 6.4 | 100 | | 99.2 |
| | 2.5 | 100 | | |
| | 2.5 | 9 | | 100 |
| 4 | 6.4 | 99.4 | — | 52* |
| | 2.5 | 99.4 | — | 23* |
| 5 | 6.4 | 81 | — | — |
| | 2.5 | 0 | — | — |
| 6 | 6.4 | 99.2 | — | — |
| | 2.5 | 18 | — | — |

*Day 27

TABLE III

Compounds of the Formula

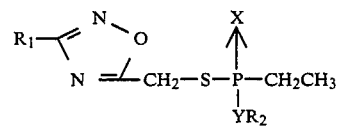

| Compound No. | X | Y | $R_1$ | $R_2$ | Concentration (ppm) | Soil Treatment % C Day 0 |
|---|---|---|---|---|---|---|
| 11 | S | O | $-CH_2CH_3$ | $-CH_2CH_3$ | 6.4 | 0 |
| | | | | | 2.5 | 0 |
| 12 | O | O | $-CH_3$ | $-CH_2CH_3$ | 6.4 | 0 |
| | | | | | 2.5 | 0 |

I claim:

1. A compound of the formula:

$$R_1 \overset{N\diagdown O}{\underset{N}{\diagup\hspace{-0.5em}=\hspace{-0.5em}\diagdown}} CH_2-S-\overset{X}{\underset{YR_2}{P}}-CH_2CH_3 \quad (I)$$

wherein X is sulfur or oxygen, Y is sulfur or oxygen, $R_1$ is methyl, ethyl, isopropyl or cyclopropyl, $R_2$ is ethyl or isopropyl provided that when $R_1$ is methyl or ethyl, then $R_2$ is not ethyl.

2. A compound according to claim 1 wherein Y is sulfur.

3. A compound according to claim 2 wherein X is sulfur, $R_1$ is methyl, and $R_2$ is isopropyl.

4. A compound according to claim 1 wherein X is sulfur, Y is oxygen, $R_1$ is ethyl, and $R_2$ is isopropyl.

5. A compound according to claim 1 wherein X is sulfur, Y is oxygen, $R_1$ is methyl, and $R_2$ is isopropyl.

6. A method for controlling corn root worms which comprises applying to the soil habitat of the corn root worms an insecticidally effective amount of a compound of claim 1.

7. A method of controlling corn root worms which comprises applying to the soil habitat of the corn root worms an insecticidally effective amount of a compound of claim 2.

8. A method of controlling corn root worms which comprises applying to the soil habitat of the corn root worms an insecticidally effective amount of the compound of claim 3.

9. A method of controlling corn root worms which comprises applying to the soil habitat of the corn root worms an insecticidally effective amount of the compound of claim 4.

10. A method of controlling corn root worms which comprises applying to the soil habitat of the corn root worms an insecticidally effective amount of the compound of claim 5.

11. A composition for controlling corn root worms comprising a biologically inert carrier and an insecticidally effective amount of a compound of claim 1.

12. A composition for controlling corn root worms comprising a biologically inert carrier and an insecticidally effective amount of a compound of claim 2.

13. A composition for controlling corn root worms comprising a biologically inert carrier and an insecticidally effective amount of the compound of claim 3.

14. A composition for controlling corn root worms comprising a biologically inert carrier and an insecticidally effective amount of the compound of claim 4.

15. A composition for controlling corn root worms comprising a biologically inert carrier and an insecticidally effective amount of the compound of claim 5.

* * * * *

UNITED STATES PATENT AND TRADEMARK OFFICE
CERTIFICATE OF CORRECTION

PATENT NO. : 4,533,658
DATED : August 6, 1985
INVENTOR(S) : WILLIAM F. KING

It is certified that error appears in the above-identified patent and that said Letters Patent are hereby corrected as shown below:

Col. 10, Table III, <u>Compound No. 12, Concentration(ppm)</u> 6.4  0, should read:

<u>Compound No. 12, Concentration(ppm)</u>  6.4   0
                                           2.5   0

Signed and Sealed this

Thirteenth Day of May 1986

[SEAL]

Attest:

DONALD J. QUIGG

Attesting Officer

Commissioner of Patents and Trademarks